United States Patent [19]

Baggen

[11] Patent Number: 5,539,755
[45] Date of Patent: Jul. 23, 1996

[54] METHOD AND APPARATUS FOR DECODING AN ERROR PROTECTED BLOCK OF EXTENDED DATA

[75] Inventor: Constant P. M. J. Baggen, Eindhoven, Netherlands

[73] Assignee: U.S. Philips Corporation, New York, N.Y.

[21] Appl. No.: 62,680

[22] Filed: May 17, 1993

[30] Foreign Application Priority Data

May 19, 1992 [EP] European Pat. Off. .............. 92201421

[51] Int. Cl.[6] ..................................... G06F 11/10
[52] U.S. Cl. ......................... 371/37.1; 371/37.7
[58] Field of Search .................... 371/37.1, 37.2, 371/37.7, 38.1, 39.1, 44, 45

[56] References Cited

U.S. PATENT DOCUMENTS

| | | | |
|---|---|---|---|
| 4,706,250 | 11/1987 | Patel | 371/38 |
| 4,890,287 | 12/1989 | Johnson et al. | 371/37.2 |
| 5,068,858 | 11/1991 | Blaum et al. | 371/41 |
| 5,268,908 | 12/1993 | Glover et al. | 371/37.1 |
| 5,379,305 | 1/1995 | Weng | 371/37.1 |

Primary Examiner—Roy N. Envall, Jr.
Assistant Examiner—Thomas E. Brown
Attorney, Agent, or Firm—Richard A. Weiss

[57] ABSTRACT

Extended error protected communication system.

An extended consumer communication system uses a signal that is error protected by a block code. The generator polynomial is $$G_n(x) = g_o(x) \ldots g_n(x)$$

which is factorizable, and each of the factors implement a linear and systematic code. Generally, each of the factors adds redundancy and raises the level of error protection. In this way, redundancy that is associated to a later term of the sequence occupies code positions that are protected by at least one earlier term in the sequence and may in consequence be used for positioning data that is protected by such earlier term, upon surrender of such higher protection level.

11 Claims, 4 Drawing Sheets

| | |
|---|---|
| $m_0(x)$ | $x+1$ |
| $m_1(x)$ | $x^7 + x^4 + 1$ |
| $m_3(x)$ | $x^7 + x^6 + x^5 + x^4 + 1$ |
| $m_5(x)$ | $x^7 + x^5 + x^4 + x^3 + 1$ |
| $m_7(x)$ | $x^7 + x^6 + x^5 + x^3 + x^2 + x + 1$ |

FIG. 4

| | $r$ | $d$ | $g_d(x)$ |
|---|---|---|---|
| $C_4$ | 8 | 4 | 8,7,5,4,1,0 |
| $C_6$ | 15 | 6 | 15,12,11,8,7,5,1,0 |
| $C_8$ | 22 | 8 | 22,20,17,13,11,9,8,6,5,3,1,0 |
| $C_{10}$ | 29 | 10 | 29,28,26,23,22,21,20,18,16,15,11,8,6,5,3,0 |

FIG. 5

| | $C_4$ | $C_6$ | $C_8$ | $C_{10}$ |
|---|---|---|---|---|
| $D_4$ | 0.0039 | 0.0039 | 0.0039 | 0.0039 |
| $D_6$ | 0.0059 | 0.0059 | 0.0059 | 0.0059 |
| $D_8$ | 0.0063 | 0.0063 | 0.0063 | 0.0063 |
| $D_{10}$ | 0.0064 | 0.0064 | 0.0064 | 0.0064 |

FIG. 6

| $C_4$ | $A(4) \approx 2482$ |
|---|---|
| $C_6$ | $A(6) \approx 2288$ |
| $C_8$ | $A(8) \approx 1055$ |
| $C_{10}$ | $A(10) \approx 282$ |

FIG. 7

|  | $C_4$ | $C_6$ | $C_8$ | $C_{10}$ |
|---|---|---|---|---|
| $D_4$ | Puncor $\approx 2^6 p$<br>Pundet $\approx 2^{11} p^4$ | Puncor $\approx 2^6 p$<br>Pundet $\approx 2^{11} p^4$ | Puncor $\approx 2^6 p$<br>Pundet $\approx 2^{11} p^4$ | Puncor $\approx 2^6 p$<br>Pundet $\approx 2^{11} p^4$ |
| $D_4$ | Puncor $\approx 2^6 p$<br>Pundet $\approx 2^6 p^3$ | Puncor $\approx 2^{11} p^2$<br>Pundet $\approx 2^{11} p^4$ | Puncor $\approx 2^{11} p^2$<br>Pundet $\approx 2^{11} p^4$ | Puncor $\approx 2^{11} p^2$<br>Pundet $\approx 2^{11} p^4$ |
| $D_4$ | Puncor $\approx 2^6 p$<br>Pundet $\approx p^2$ | Puncor $\approx 2^{11} p^2$<br>Pundet $\approx 2^{11} p^4$ | Puncor $\approx 2^{15} p^3$<br>Pundet $\approx 2^{11} p^4$ | Puncor $\approx 2^{15} p^3$<br>Pundet $\approx 2^{11} p^4$ |
| $D_4$ | Puncor $\approx 2^6 p$<br>Pundet $\approx 2^{-8} p$ | Puncor $\approx 2^{11} p^2$<br>Pundet $\approx 2^2 p^3$ | Puncor $\approx 2^{15} p^3$<br>Pundet $\approx 2^{11} p^4$ | Puncor $\approx 2^{19} p^4$<br>Pundet $\approx 2^{11} p^4$ |

FIG. 8

METHOD AND APPARATUS FOR DECODING AN ERROR PROTECTED BLOCK OF EXTENDED DATA

BACKGROUND OF THE INVENTION

The invention relates to a transmitter-receiver communication system which uses an extended communication signal encoded according to a digital encoding standard and comprising dam that is covered by an error protection block code. Various systems are known that use such extended communication signal encoded according to a digital encoding standard, such as the Compact Disc standard for hifi audio, and the extended version thereof, CD-ROM, that offers a higher degree of error protection for sensitive data. At present, television signals also being standardized according to a bit-based format. Such standardization often evolves through extended contacts between various manufacturers, governments, public bodies, and others. Besides standards for consumer communications, standards for professional communications have come into existence as well. Generally, the format has user bits and control bits, but this is not a prerequisite. The term "extended" indicates that the system allows for communicating more information than the minimum, thereby allowing additional physical, logical, or notional channel capability. Physical means additional data, such that the user would experience a higher throughput. Logical means that additional data is transferred that borrows its relevance from the main data, such as a time indication that could be made accessible to the user or be used for enabling easier random access when the data is stored in a memory. Notional means that the functionality of the additional data is transparent to the user, such as when it would allow the system an improved functionality. Various other possibilities exist.

The data content of the user bits is unpredictable, but their prescribed minimum amount is given. As a result, their existence is taken for granted.

Often, the extension bits are used on a system level, to signal, at the receiver side certain general properties of the signal organization. Such properties, without any limitation in the following recitation, may relate to the coding format of the associated user information, additional user information that may be added to the main user information according to discretion, frame numbering or time indication, or information that is self-referencing to the control information proper.

When a new standard for a communication signal, supra, is first set up, various ones of the control bits are left undefined but kept in reserve for possible later definition. In addition, the need has emerged for error protection of the control bits or other extension bits against burst and/or random errors. By itself, error protection block codes are well known. With respect to protection of the extension bits, certain ones of which have been defined according to some standardization or assignation protocol, whereas others are not (yet) so defined, and, as a result, can from the level of the control be considered as dummy or spare bits, there are various different possibilities. A first possibility is to set all undefined bits equal to zero and to have an error correction scheme cover both defined and undefined bits. However, the inventor has recognized that this amounts to throwing away transfer and error protection capability of the channel. Another aspect is to allow for a variable error correcting code (ECC) strategy to cope with known channel quality variations, i.e., the decoder should be allowed to decide which level of error protection to be applied.

SUMMARY OF INVENTION

It is, inter alia, an object of the present invention to provide a unitary protection format for defined control bits that offers an elevated protection level, while retaining space for later definable bits that would also have a particular error protection level which will leave part of the error protection of the earlier defined bits operational.

According to one of its aspects, the invention provides a communication system according to the preamble that is characterized in that the block code is a self-contained and hierarchically nested code through the use of an associated generator polynomial that is factorizable as a series of factors:

$$G_n(x) = g_o(x) \ldots g_n(x),$$

wherein the code is a linear code. Any generator polynomial of the sequence $G_o(x), \ldots G_n(x)$ defines a systematic code, and any code generated by $G_{j+1}(x)$ provides a higher protection level than the code generated by $G_j(x)$ as far as both $j$ and $(j+1)$ are in the interval, so that part of the redundancy information associated to a later term of the sequence occupies code positions that are protected as non-redundant information by at least one earlier term of the sequence and may in consequence be used for positioning data that is protected by such earlier term upon surrender of the higher protection level. The system allows receiver-sided decoding as based on $G_j(x)$ or $G_{j+1}(x)$. Upon later usage of redundancy bits associated with later terms of the sequence for other purposes, the error protection offered by earlier terms of the sequence remains operational. Although n may have arbitrary integer values, at least 2 is advantageous, for this means that two successive levels of protection may be surrendered. The format is furthermore self-contained, thereby not needing external indication on the effectively present level of protection. Such external indication could itself be subject to errors. According to the invention, the structure of a code block itself would indicate whether it has a higher, or, alternatively, lower degree of error protection. The code as defined above is not a concatenated code. (Upon decoding a concatenated code each decoding level is fully evaluated before the next level decoding can be undertaken.) In the next level, the redundancy related to the preceding level is completely left out of consideration. According to the present invention, the codes used by necessity belong to a single mathematical class and no information outside the code block need be accessed to indicate the applicable protection level.

Advantageously, the data is control data that is ancillary to user data in the signal that is not covered by the code. Often, the amount of user data is large with respect to the amount of control data. The user data may be digital, such as teletext. It could even be analog signalization, such as a conventional television signal. The coding according to the invention is particularly advantageous when the amount of data is small. On the other hand, large quantities of data may also be protected by the codes according to the present invention.

Advantageously, the code is a BCH-code. BCH-codes have a well established theory both on their generation as well as on their decoding. The hierarchical character of the present code lends then a particular character. Advantageously, the code is binary, which is used in the embodiment hereinafter. On the other hand, multi-bit symbols could be used, such as Reed-Solomon codes. The choice could be made on the basis of a fault model. For random bit errors the binary codes are preferred.

Advantageously, the factors $g_o(x), \ldots g_n(x)$ are minimal polynomials. Minimal polynomials are those that have minimal degree for attaining a particular distance as given by the lowest degree of the polynomial that contains the intended power of $\alpha$. This also results in a minimum amount of redundancy. On the other hand, in certain situations decoding is easier for a non-minimal polynomial.

Advantageously, each generator polynomial $G_j(x)$, wherein $j \leq 2$ defines a number of equally spaced zeroes of $G_n(x)$. The zeroes may be consecutive zeroes, alternatively, their spacing could be uniform by two, three, or more positions. This leaves the index of the minimal polynomials open. By itself, such a uniform structure is easier to decode and better accessible to coding theory (and thus easier to predict as to its effective protectivity).

Advantageously, for minimal binary BCH-codes, the generator polynomial is $$G_n(x) = m_1(x) * m_3(x) \ldots * m_{2n+1}(x)$$

with each polynomial $G_{2j+1}(x)$ allowing an additional error to be corrected over such error correction as realizable through $G_{2j-1}(x)$, provided that $m_{2j+1}(x)$ introduces an additional zero into the generator polynomial $G_{2j+1}(x)$. It has been found that it is advantageous that stepping up the level of protection should mean increasing the level of correctability. The first term may well relate to a CRC-code. These are well-known and easy to implement. It should be noted that in this particular generator polynomial, the zero covered by $m_9(x)$ is also covered by $m_3(x)$, so that the former would not increase the distance of the code. The same applies to even-numbered minimal polynomials.

Advantageously, the code is based upon a generator polynomial $$G_n(x) = (x-1)^k * G_n(x)$$

wherein $k \leq n+1$, with each of the k factors $(x-1)$ being co-encoded with an exclusive one of the factors, starting with the first (n=0). Combining factor $m_1(x)$ with a factor $(x-1)$ increases the distance of these paired factors. The combination of further higher-numbered factors with the same factor $(x-1)$ does not increase the distance per se, but still enhances the capacity for correcting burst errors in a binary code.

In particular, the signal may be a broadcast signal for digital television. A favorite line is first half No. 23 in the PALPLUS format for positioning the extended consumer communication signal in question. It should be noted that the standardization question as touched above is especially in consumer systems a hot item (upgrading system capability should not instantaneously require new user terminals).

The invention also relates to a method of encoding an extended communication signal as defined earlier.

The invention still further relates to a decoder for decoding such as extended communication signal, in particular being arranged for generating either an O.K. signal upon completion of a correction operation, or an -unfeasible-signal under control of either an uncorrectable error for the decoder in question detected, or an error outside the correctable range of the code received. This set-up is advantageous in various aspects. The decoder correctly signals that it cannot handle the error pattern. The problem then may reside either in a code having too small a distance, or in a decoder that has insufficient capability. Of course both cases may occur simultaneously. The decoder need not know in advance the distance of a code received, and in fact, may receive intermixed codes that have non-uniform distances.

Various further advantageous aspects of the invention which become apparent from the discussion which follows.

DETAILED DESCRIPTION OF THE PREFERRED EMBODIMENTS

Various error protecting codes like CRC (cyclic redundancy checks) and, Hamming codes and many multiple error correcting codes can be described as BCH codes. Generally, however, the invention is applicable to BCH codes that have a factorizable polynomial. As always, the effective choice among the gamut of codes is made based on fault model, size of the block, required level of error protection and ease of the decoding. In, the remainder, a code word (a string of bits) of length n is represented as a polynomial in the indeterminate quantity x, i.e., $$(c_0, c_1, \ldots, c_{n-1}) \Leftrightarrow c_0 + c_1 x + \ldots + c_{n-1} x^{n-1} = \sum_{i=0}^{n-1} c_i x^i := c(x),$$

where $c_i \in \{0,1\}$. The power i of $x^i$ serves as a position indicator of bit $c_i$. Likewise a received word (possibly containing errors) is represented as r(x). The specific example discussed hereinafter relates to binary BCH-codes. However, the invention also applies to non-binary BCH-codes such as Reed-Solomon codes, and even to non-BCH-codes.

BCH codes are cyclic codes, and they are characterized by the fact that each code word c(x) is a multiple of a generator polynomial g(x). This fact is used for encoding and decoding BCH codes. For instance, in checking a CRC, the received word r(x) is fed through a feedback shift register, which in mathematical terms is equivalent to dividing (in the Galois Field GF(2)) the received word by the polynomial that is represented by the feedback connections of the feedback shift register. If the remainder is zero (CRC=OK), the received word is a multiple of g(x):

r(x) mod g(x)=0, i.e., the received word belongs to the code. If the remainder is not zero, an error is detected. Depending on the properties of the code, errors can be corrected by applying mathematical operations to this remainder.

The error detecting and correcting properties are determined by the factors of the generator polynomial, i.e., in our case g(x)=$m_0(x)m_1(x)m_3(x) \ldots$, where each factor $m_i(x)$ is itself a polynomial. The factors themselves may be minimal and, thus, have the lowest amount of redundancy that is commensurate with the intended distance of the code. The factors may be irreducible or may be a product of irreducible polynomials. A particular factor may be $m_0(x)=(x+1)$, which corresponds to a single overall parity check if $c(x)$ is divisible by $(x+1)$. Polynomial $g(x)$ can have multiple factors, whereby the error correcting capability generally increases if more factors are included.

An exemplary CRC-8 is defined by:

$$g(x)=g_4(x)=(x+1)m_1(x),$$

where $m_1(x)$ is a degree seven primitive polynomial over GF(2). The degree of $g_4(x)$ equals eight and is equal to the number of parity bits. BCH theory shows that the minimum distance d of this code $C_4$ equals four, provided that the code word length does not exceed 127. The distance of the generated code is indicated by the subscript of C and the subscript of its generator polynomial g. The code $C_4$ generated by $g_4(x)$ detects any error pattern of weight less than or equal to three. It may alternatively correct a single error and detect simultaneously all double errors.

If $m_3(x)$ of degree seven is added to $g_4(x)$, a code $C_6$ is obtained, which code is generated by:

$$g_6(x)=m_3(x)g_4(x),$$

which is a subcode of the code generated by $g_4(x)$, i.e., the code words belonging to $C_6$ are a subset of the code words belonging to $C_4$. The error correcting capability increases to two bit error correction or five bit error detection, again provided that the code word length does not exceed 127. The addition of $m_3(x)$ to the generator polynomial means that seven more parities must be stored, i.e., $C_6$ has 15 parity bits.

An alternative possibility is:

$$g'_6(x)=(x+1)m_3(x)g_4(x).$$

which needs 16 parity bits and has two coinciding zeroes at $x=-1$. Note that for a BCH-code defined over a field of characteristic 2, the factors $(x-1)$ and $(x+1)$ are identical. Likewise codes $C_8$ and $C_{10}$, can be constructed which codes are generated by:

$$g_8(x)=m_5(x)g_6(x) \text{ and} \quad (1)$$

$$g_{10}(x)=m_7(x)g_8(x), \quad (2)$$

having 22 and 29 parity bits respectively. The relationships between the nested codes are given by:

$$C_4 \supset C_6 \supset C_8 \supset C_{10}$$

In general a code $C_d$, generated by $g_d(x)$, can correct t and detect simultaneously any number of e ($e \geq t$) errors provided $$t+e<d.$$

It is noted that the balance between t and e in an actual situation is dependent on the required detection and miscorrection probabilities. Using the weight distribution of the codes involved, these can be calculated.

Figure 1A:
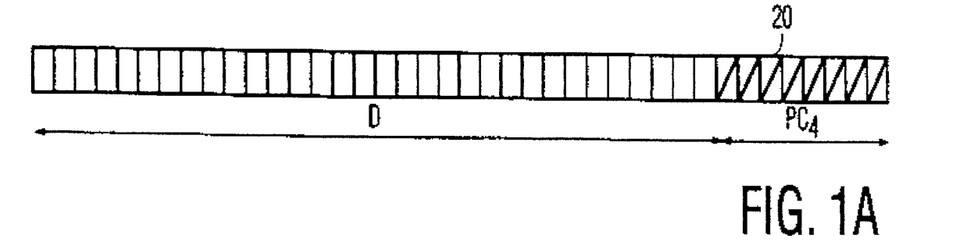
FIGS. 1A–D show configurations of various code words.

FIGS. 1A–D show the format of 40 bit code words in accordance with the $C_4$, $C_6$, $C_8$ and $C_{10}$ codes, respectively. FIG. 1A shows a 40 bit code word of the $C_4$ code made up of 32 data bits D and 8 parity bits 20 of a CRC code (the error protection capability thereof having been described earlier).

Figure 1B:
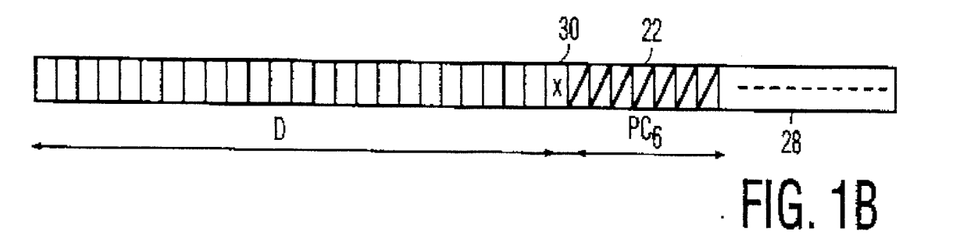

FIG. 1B shows a code word of the $C_6$ code. It has 15 parity bits, i.e., 7 additional parity bits 22, and 24 data bits D. Part 28 indicates the parity bits of the code $C_4$, which in FIG. 1B are also used to raise the level of error protection. A single bit 30 can be used for various objects. First, it can be data that is error protected at this level. Going to the next higher protection level may lead to a shift over 8 bits of the boundary between data and parity, which is easy for calculation. At this higher level, bit 30 would then be a dummy bit. Another solution is a shift of the boundary over seven bits, which keeps as much data available as possible, but complicates calculations in an 8-bit processor. A third solution is to add another factor $(x+1)$ to the generator polynomial. This does not increase the distance of the code (double use of the same factor polynomial), but improves the error correction and detection capacity against burst errors.

Figure 1C:
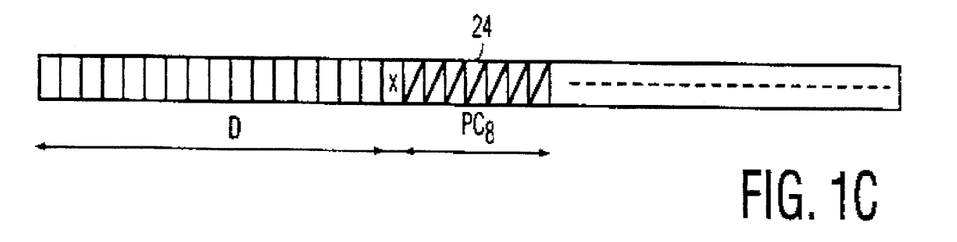

FIG. 1C shows the format of a C8 code word that has 16 data D bits, and and 22 parity bits, i.e., an additional 7 parity bits.

Figure 1D:
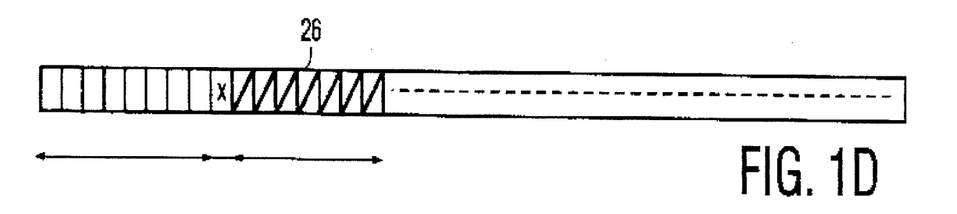

FIG. 1D shows the format of a C10 code word. Using the three bits indicated by small crosses would increase the maximum available data to 11 bits at the most protected level, at the price of rather irregular processing requirements. Of course, the nesting organization according to the present invention may be done at other modularity steps, wherein the module preferably is a power of 2. Of course, the 40 bit code word format is only one of many possibilities.

Figure 2:
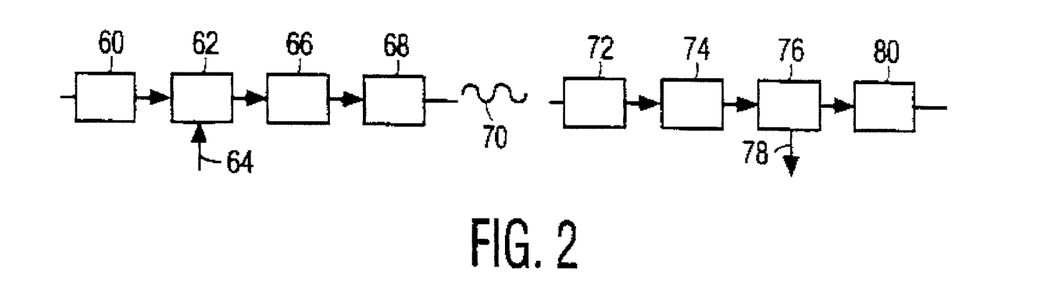
FIG. 2 shows an overall block diagram of the system.

FIG. 2 is an overall block diagram of the system. Block 60 provides the user data. For television, it may, for example, comprise the picture itself, various synchronization signals and additions, such as teletext. In block 62, various particular dam may be added, such as control dam, along input 64. It is feasible that either these particular dam, or all data are protected according the teachings of the present invention. There may be various different levels of error protection according to the present invention at any one time. In block 66 the actual error protection is provided, such as by matrix multiplication or other techniques. In block 68 any remaining operation for the transmission may be effected, such as conversion to channel bits and modulation with carder frequencies and the like. After broadcast 70, block 72 recaptures the transmitted dam through demodulation. Block 74 recognizes those fractions of the data that are error protected and effects error protection, as will be described hereinafter. In block 76, the control data is separated from the main stream according to arrow 78. In block 80, user data is rendered presentable to a user, such as by display, hard copy, or otherwise.

Both at the encoding side and at the decoding side, all operations may be mapped on common hardware. At the decoding side, this may be standard hardware that is suitably programmed, such as an 8-bit microcontroller. For volume manufacture, specially designed hardware may be used.

A particular advantage of the above described this set of nested codes is that a code $C_i$ can be decoded by the decoder of all codes $C_j$, $j \leq i$, up to the distance of $C_j$. For example, if the actual code transmitted is generated by $g_6(x)$, the CRC-8 can still be checked, since a multiple of $g_6(x)$ certainly is a multiple of $g_4(x)$. The concept of nested codes allows a redefinition of bits and codes in a later stage without backward compatibility problems.

It is assumed that initially when only a few information bits have been defined, the code $C_{10}$ is used. If somewhere in the future more information bits are needed and channel conditions turn out to be favorable, the transmitted code can be changed from $C_{10}$ to $C_8$, thereby gaining seven or eight more information bits, of course with less error protection. In another later stage, the code can be changed from $C_8$ to $C_6$ and once more from $C_6$ to $C_4$, each time gaining another seven or eight information bits. With $C_4$, the CRC-8 has been reached, and the number of parity bits cannot be reached anymore without severely compromising reliability. Hence the CRC-8 can be used for all codes.

The effective decoder chosen at the receiver side may be codetermined by cost considerations. In fact, often an independent selection is possible, which is given by way of example. For instance, one could opt for only checking the CRC-8, although the code $C_{10}$ is transmitted. Or one could build a decoder that corrects at most a single error while $C_{10}$ is transmitted.

Figure 4:
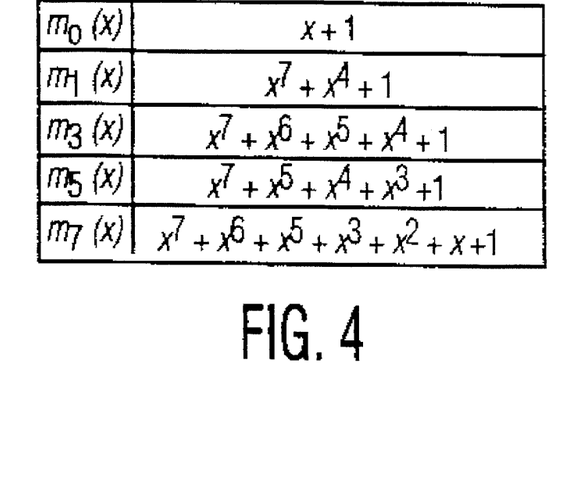
FIG. 4 shows a Table: 1 minimal polynomials.
Figure 5:
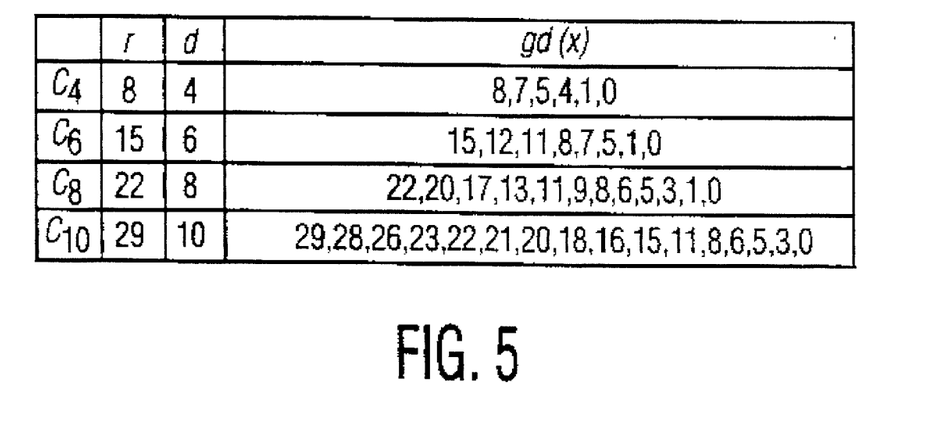
FIG. 5 shows a Table: 2 nested BCH-codes with primitive block length 127.

In Table 1 (See FIG. 4), a list is given of the required minimal polynomials for constructing the code. In Table 2 (see FIG. 5), a list is given of the nested codes, indicating for each code the number of parity symbols r, the distance d and the generator polynomial of the code. The generator polynomial is given by the powers of x that are present in g(x), i.e., $$x^8+x^7+x^5+x^4+x+1 \Leftrightarrow 8,7,5,4,1,0$$

Since the receiver does not know the actual distance of the code, a decoding strategy needs to be defined. The decoding strategy results in about the same acceptable probabilities for undetected error as while using the CRC-8, but with greatly improved probabilities for correct reception in case the actually transmitted code has a higher distance.

A possible decoding strategy is presented hereinafter in the form of a pseudo language. It is presumed that the generator polynomial g(x) is a product of minimal polynomials $m_0(x)$, $m_1(x)$ and an unknown number of other irreducible factors so that in each successive nested layer the designed distance increases by 2. Upon reception, the syndromes are defined according to:

$$S_j = r(x) \bmod m_j(x),$$

i.e., $S_j$ the remainder of dividing the received word r(x) by $m_j(x)$. Given a number of syndromes $S_j$, the corresponding error pattern can be calculated using the BCH decoding algorithm. The outcome of this algorithm is either an estimated error pattern with a corresponding Hamming weight t (which can be zero if there were no errors at all), or an uncorrectable error pattern if the (algorithm fails). The decoding strategy can be seen as a tree with nodes and leaves. The nodes are labelled by the distance d that is considered by the decoder at that point. The following is the procedure for executing the tree of the decoding strategy:

```
Begin (node 4)
    calculate S₀
    calculate S₁
    estimate error pattern (test if S₀ and S₁ are zero)
    if t=0
        then OK, exit
        else (node 6)
            calculate S₃
            estimate error pattern (try single error correction)
            if t=1
                then correct, OK, exit
                else (node 8)
                    calculate S₅
                    estimate error pattern (try double error correction)
                    if t=2
                        then correct, OK, exit
                        else (node 10)
                            calculate S₇
                            estimate error patten (try triple error correction)
                            if t=3
                                then correct, OK, exit
                                else ERROR, exit
end
```

The exit attained after ERROR signalization means that either the number of errors was greater than correctable with this particular decoder implementation, or, alternatively, was greater than correctable with the actually implemented code. In the latter case, the decoder may or may not have been able to tackle the actually encountered error pattern.

Note that a decoder implementation need not search the whole tree. After each "else", the decoder can quit with the outcome ERROR if the required operations in the next node are not implemented. For instance, for a simple CRC-8 checker, the item—(node 6)—is changed into —ERROR, exit—, whereas the lines from —calculate $S_3$—(up through the penultimate line, are deleted. For a single-error corrector, in the above—(node 8)—is changed into —ERROR, exit—, whereas all lines from —calculate $S_5$—up through the penultimate line, are deleted.

Figure 3:
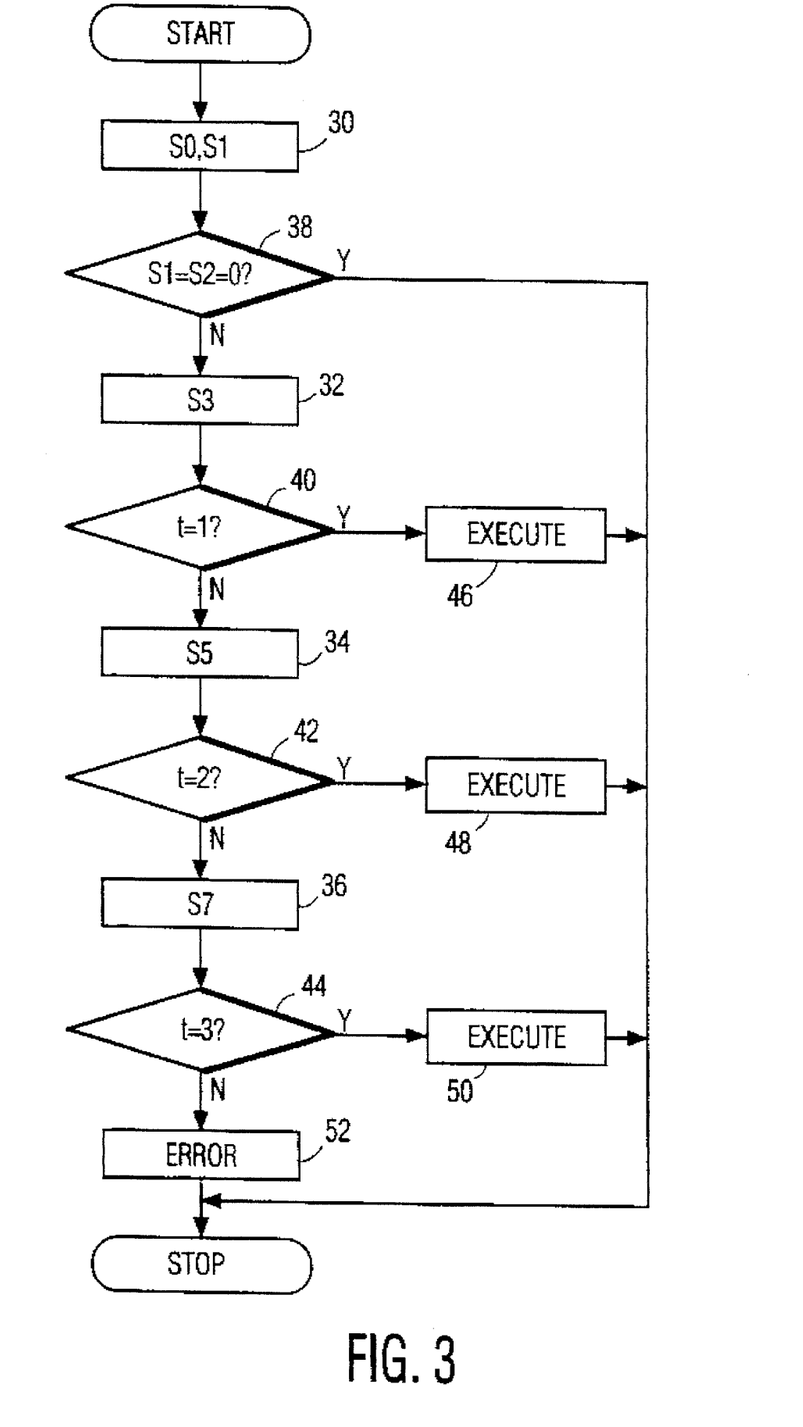
FIG. 3 shows a flow chart of the decoding operations.

FIG. 3 gives the above procedure in a flow chart. Blocks 30, 32, 32, 34 and 36 calculate the syndromes as necessitated. Blocks 38, 40, 42 and 44 test for actual presence of respective predetermined numbers of errors (0, 1, 2, 3, respectively). Blocks 46, 48 and 50 execute the proper correction. Block 52 signals an effective error.

Various other strategies may be adopted, dependent on the factorization, estimated error probabilities, available hardware, and others. The step in distance provided by the additional factors may be different. In principle, a distance increase of one would be feasible, but at least two is preferred. This increase need not be uniform over the sequence of factors. One or two levels could be executed on-line, whereas higher protection may need recourse to a background processor.

Hereinafter, the performance of decoding will be evaluated for each of the above combinations of a code $C_4 \ldots C_{10}$ and a decoder $D_4 \ldots D_{10}$, using the method described with respect to FIG. 2, and looking to both random errors and burst errors:

$D_4 := t=0$, using $S_0$ and $S_1$;
$D_6 := $ up to t=1, using $S_0$, $S_1$ and $S_3$;
$D_8 := $ up to t=2, using $S_0$, $S_1$, $S_3$ and $S_5$; and
$D_{10} := $ up to t=3, using $S_0$, $S_1$, $S_3$, $S_5$ and $S_7$.

The performance is expressed as an uncorrected error rate $P_{uncor}$ (probability that a decoder cannot correct the received word) and an undetected error rate $P_{undet}$ (probability that the decoder wrongly corrects or does not detect an error pattern). The decoding strategy can be considered as a tree, where each node that is visited by decoder $D_i$ has a separate contribution to the resulting $P_{uncor}$ and $P_{undet}$ of that particular decoder, depending on the probability of the decoder reaching that node and the conditional probabilities (conditioned on the decoder reaching that node) of the decisions taken at that node.

Figure 6:
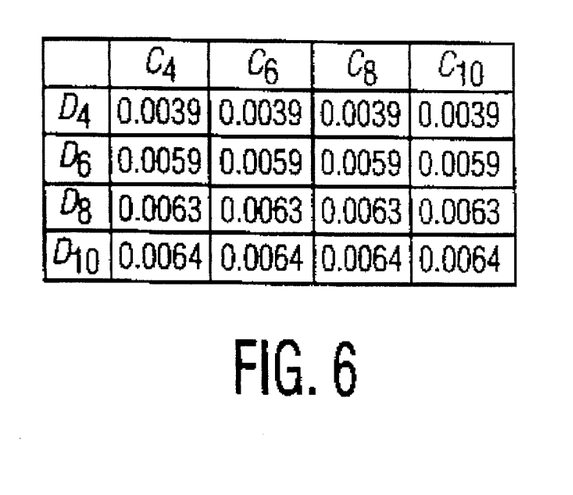
FIG. 6 shows a Table: 3 probability of undetected error for bursts.

For burst errors, we assume that the size of the burst is such that the syndrome can be considered as being random. The desired response of all decoders in all instances should be a detection of an uncorrectable error pattern. All other outcomes, in which a decoder (wrongly) accepts or corrects the received word, are defined as an undetected error. Table 3 (see FIG. 6) indicates the probability of such undetected errors for each possible code and decoder pair, given that a large burst has occurred, i.e., probabilities conditioned on the occurrence of a burst. The probability for a undetected error of a sufficiently large burst only depends on the decoding strategy, not on the code, since the received pattern is considered to be random. For a node, assuming r parity bits and estimating an error pattern of weight t, the contribution is given by:

$$\Delta p_{undet} \approx 2^{-r} \binom{n}{t},$$

i.e., the fraction of randomly chosen syndromes that correspond to a correctable error pattern given the first r syndrome bits. Table 3 is constructed using n=64. Note that for a first order approximation $$p_{undet}(D_{10})=\Delta p_{undet}(node4)+\Delta p_{undet}(node6)+\Delta p_{undet}(node8)+\Delta p_{undet}(node10).$$

Likewise, the other entries can be calculated.

Figure 8:
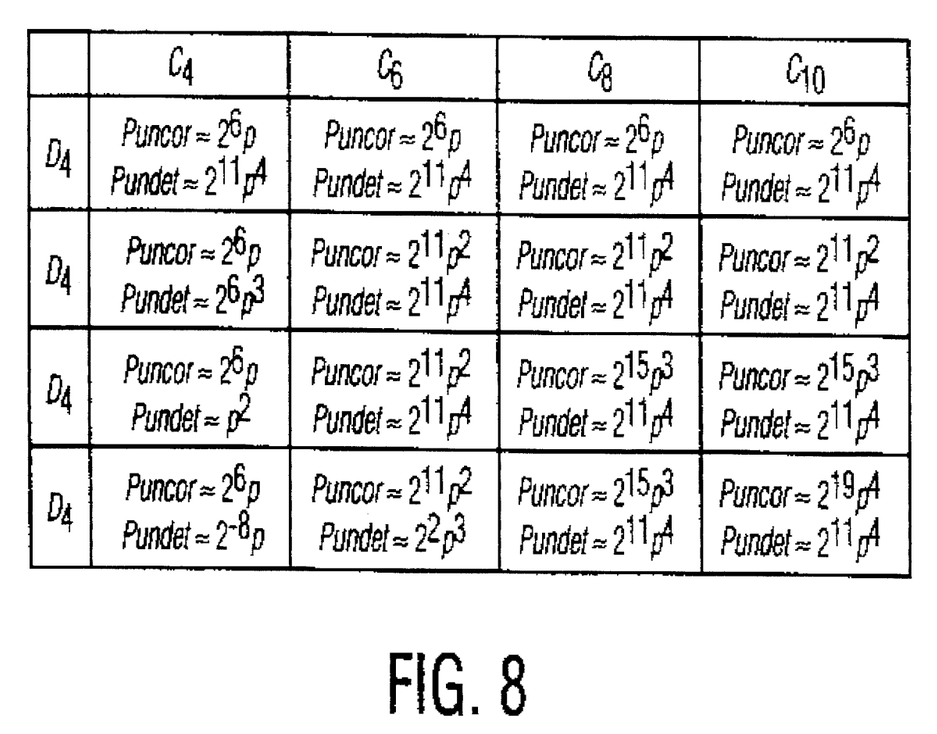
FIG. 8 shows a Table: 5 probability of error for random errors.

Table 5 (see FIG. 8) indicates for each possible code and decoder pair the first order approximation to the uncorrected and undetected error probability, assuming random bit errors with (small) bit error probability p. In order to evaluate the performance, we must distinguish between a number of node situations.

The first node situation is where the code $C_d$ and the current decoding attempt are matched with respect to the distance d, i.e., the transmitted code has r parity bits and the decoder considers also r parity bits. This corresponds to the traditional way of evaluating the performance of a code. For a linear code $C_d$ having length n, minimum distance d and a number A(d) words of weight d, the probability of an uncorrected error assuming t error correction is (first order estimation)

$$\Delta p_{uncor} \approx \binom{n}{t+1} p^{t+1}, p << 1.$$

Furthermore, the probability of an undetected error can be approximated by:

$$\Delta p_{undet} \approx A(d) \binom{d}{t} p^{d-t}.$$

Figure 7:
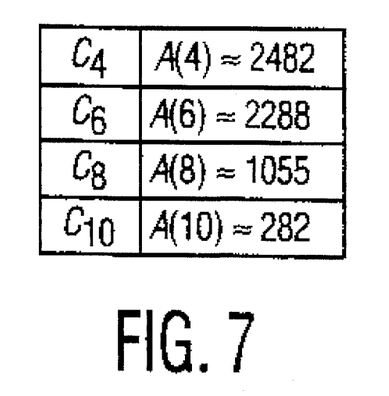
FIG. 7 shows a Table: 4 estimation of minimum weight code words.

It is assumed that the weights are binomially distributed for weights larger than or equal to d, i.e., $$A(d) \approx 2^{-r} \binom{n}{d},$$

where r is the number of parity bits of the code. Since x+1 is a factor of g(x) for all codes, A(w)=0 for odd w. Assuming n=64, a list of minimum weight code words is obtained as given in Table 4 (see FIG. 7).

The second node situation is where the distance of the actual transmitted code is larger than the distance considered by the decoder at that node, i.e., $C_d$ being transmitted has r parity bits, while at the current node r'<r bits are considered. In that case, the decoder is unaware of the extra constraints on the code, and it considers only the zeroes of g(x) that correspond to the first r' parity bits. Hence the performance of error correction and error detection is the same as if $C_{d'}$, corresponding to r' parity bits would have been transmitted. In case of an uncorrectable error pattern at a particular node, the next node will be visited with probability $1-\Delta p_{undet}$, if that node has been implemented in the decoder. If not, an error is detected.

In the third node situation, a decoder attempts to decode $C_d$ beyond its designed distance. The only correct outcome of decoding attempts in such a situation should be a decoding failure, since a correctable error pattern should have been corrected in one of the foregoing nodes. The uncorrectable error rate is determined by $C_d$, since up to distance d, consistent results can be obtained by considering the zeroes of the generator polynomial. However, if the decoder evaluates the received word in a nonexisting zero of the code, the result will be a random seven bit pattern (with a probability of $2^{-7}$ that it is consistent with a given error pattern), if we assume that all code words are equally likely.

This result can easily be shown by counting arguments. Consider for instance the standard array of $C_6$ which has $2^{15}$ cosets. Each coset corresponds to a particular syndrome. The syndrome (15 bits) may be partitioned in $S_0$ (1 bit), $S_1$ (7 bit) and $S_3$ (7 bit). Since any fifteen bit pattern occurs exactly once, there is exactly one coset for each value of $S_3$ and $S_0=S_1=0$. Since the code $C_4$ consists of the union of the cosets having $S_0=S_1=0$, the code $C_4$ is partitioned in sets of equal size with respect to the value of $S_3$. Since it is assumed that each code word has the same likelihood of being transmitted and the calculation of a remainder is a linear operation, the uniform outcome of the remainder in a nonexisting zero has been shown.

Decoding attempts beyond the designed distance adds nothing to the correcting capabilities ($p_{uncor}$), but noes have a detrimental effect on $p_{undet}$, since a detected error might seem correctable after all. The contribution to $p_{undet}$ at node d+2 is equal to a first order approximation $$\Delta p_{undet} \approx 2^{-7} \left[ A(d) \binom{d}{t} p^{d-t} \right],$$

where t is the number of errors that the decoder tries to correct at node d+1. Likewise, the contribution to $p_{undet}$ at node d+4 in first order approximation is $$\Delta p_{undet} \approx 2^{-14} \left[ A(d) \binom{d}{t} p^{d-t} \right],$$

where t is the number of errors that the decoder tries to correct at node d+1.

I claim:

1. A method of decoding an error protection block of extended data to produce a user block of user data, the error protection block having been produced by (a) encoding an original user block of user data by a linear and systematic primary error protection block code defined by a factorizable generator polynomial $$G_n(x)=g_0(x) \ldots g_{n-1}(x)*g_n(x)=G_{n-1}(x)*g_n(x)$$

if the original user block had a first length, or (b) encoding the original user block by a linear and systematic secondary error protection block code defined by a generator polynomial $$G_{n-1}(x)=g_0(x) \ldots g_{n-1}(x)$$

if the original user block had a second length which was greater than the first length, the error protection block being the same length whether the original user block which was encoded to produce it had the first length or the second length, the method comprising:

decoding the error protection block in accordance with the secondary code to produce a first decoded block;

detecting whether the first decoded block contains correct user data, and if it does, outputting the first decoded block as the user block; and decoding the error protection block in accordance with the primary code to produce a second decoded block if the first decoded block does not contain correct user data, and thereafter, outputting the second decoded block as the user block.

2. The decoding method as claimed in claim 1, wherein the primary and secondary codes are BCH codes.

3. A decoder for decoding an error protection block of extended data to produce a user block of user data, the error protection block having been produced by (a) encoding an original user block of user data by a linear and systematic primary error protection block code defined by a factorizable generator polynomial $$G_n(x) = g_0(x) \ldots g_{n-1}(x) * g_n(x) = G_{n-1}(x) * g_n(x)$$

if the original user block had a first length, or (b) encoding the original user block by a linear and systematic secondary error protection block code defined by a generator polynomial $$G_{n-1}(x) = g_0(x) \ldots g_{n-1}(x)$$

if the original user block had a second length which was greater than the first length, the error protection block being the same length whether the original user block which was encoded to produce it had the first length or the second length, the method comprising:

- first decoding means for decoding the error protection block in accordance with the secondary code to produce a first decoded block;
- detection means for detecting whether the first decoded block contains correct user data;
- second decoding means for decoding the error protection block in accordance with the primary code to produce a second decoded block if the first decoded block does not contain correct user data; and
- means for outputting the first decoded block as the user block if it contains correct user data, or the second decoded block as the user block if the first decoded block does not contain correct user data.

4. The decoder as claimed in claim 3, further comprising control means for activating said first decoding means and said detection means in sequence and, if necessary, said second decoding means thereafter.

5. The decoder as claimed in claim 3, wherein said first decoding means is adapted to correct a first amount of errors and detect a second amount of errors which is greater than the first amount of errors.

6. The decoder as claimed in claim 3, wherein said first and second decoding means utilize common hardware.

7. The decoder as claimed in claim 3, wherein the primary and secondary codes are BCH codes.

8. A transmitter-receiver communication system, comprising:

an encoder, including
receiving means for receiving a user block of user data having either a first length or a second length, where the second length is greater than the first length;

first encoding means for encoding the user block by a linear and systematic primary error protection block code defined by a factorizable generator polynomial $$G_n(x) = g_0(x) \ldots g_{n-1}(x) * g_n(x) = G_{n-1}(x) * g_n(x)$$

to produce the error protection block if the user block has the first length; and second encoding means for encoding the user block by a linear and systematic secondary error protection block code defined by a generator polynomial $$G_{n-1}(x) = g_0(x) \ldots g_{n-1}(x)$$

to produce the error protection block if the user block has the second length;

wherein the error protection block produced by either said first encoding means or said second encoding means has the same length; and a decoder, including:

- first decoding means for decoding the error protection block in accordance with the secondary code to produce a first decoded block;
- first detection means for detecting whether the first decoded block contains correct user data;
- second decoding means for decoding the error protection block in accordance with the primary code to produce a second decoded block if the first decoded block does not contain correct user data; and
- means for outputting the first decoded block if it contains correct user data or the second decoded block if the first decoded block does not contain correct user data.

9. The system as claimed in claim 8, further comprising a set of spatially distributed transmitter stations collectively fed by said receiving means, wherein said first encoding means is situated in each of a first subset of said set and said second encoding means is situated in each of a second subset of said set, said first and second subsets being mutually exclusive.

10. The system as claimed in claim 8, further comprising a set of spatially distributed transmitter stations collectively fed by said receiving means, wherein said first encoding means is situated in each of a first subset of said set and said second encoding means is situated in each of a second subset of said set, said first and second subsets being mutually overlapping.

11. The system as claimed in claim 8, wherein the primary and secondary codes are BCH codes.

* * * * *